United States Patent [19]
Young et al.

[11] Patent Number: 5,782,783
[45] Date of Patent: Jul. 21, 1998

[54] ORTHOSIS FOR THE UPPER BODY

[75] Inventors: David Ernest Young, Watlington; Colin Alfred Young, Abingdon, both of United Kingdom

[73] Assignee: Protectair Limited, Abingdon, England

[21] Appl. No.: 904,123

[22] Filed: Jul. 31, 1997

Related U.S. Application Data

[63] Continuation of Ser. No. 508,137, Jul. 27, 1995, abandoned.

[30] Foreign Application Priority Data

Feb. 16, 1995 [GB] United Kingdom ............... 9502988

[51] Int. Cl.[6] ........................................... A61F 5/00
[52] U.S. Cl. ........................................ 602/20; 602/19
[58] Field of Search .............................. 128/877, 878, 128/881; 602/4, 5, 16, 19–21

[56] References Cited

U.S. PATENT DOCUMENTS

| | | | |
|---|---|---|---|
| 4,259,949 | 4/1981 | Axelsson | 602/20 |
| 4,417,569 | 11/1983 | Brudny | 602/20 |
| 4,651,719 | 3/1987 | Funk et al. | 602/20 X |
| 5,385,536 | 1/1995 | Burkhead et al. | 602/20 |

*Primary Examiner*—Linda C. Dvorak
*Attorney, Agent, or Firm*—Tilton Fallon Lungmus

[57] ABSTRACT

An orthosis for the upper body is provided for controlling the shoulder and the arm. The orthosis employs a connection between the waist band and the upper part of the orthosis, specifically a lateral upright, which has two linked joints. Preferably, the lower joint is attached centrally to the waist band and is a spherical zone joint which accommodates bending at the waist and variation in the shape of the torso. The second joint is a pivot joint which accommodates rotation about an axis parallel to the long axis of the lateral upright upon the lower end of which, preferably, it is mounted.

4 Claims, 5 Drawing Sheets

ORTHOSIS FOR THE UPPER BODY

This is continuation of application Ser. No. 08/508,137, filed Jul. 27, 1995, now abandoned.

BACKGROUND AND SUMMARY

This invention relates to orthoses which are used on the upper body, such as shoulder braces.

Bracing of the upper body is now widely practiced and in many procedures there is a requirement, following injury or surgery, to rehabilitate the shoulder in a particular fixed position or with a restricted range of motion. Because of the rapid growth in sophisticated shoulder surgery, particularly by the arthroscopic method, surgeons have recently begun to seek more complex rehabilitative bracing solutions.

Formerly, traditional slings made from bandages or stockinet or abduction pillows were generally regarded as adequate. Nowadays, this is frequently not the case and several shoulder braces have been introduced in the last few years which offer restricted range of motion in some or all of abduction, flexion, extension and rotation; in addition many offer control of motion of the arm and the elbow joint.

Many modern shoulder braces have a number of structural elements in common. Typically there is a lateral member disposed as an upright strut which is attached, at its lower end to a waist band and near its upper end to a chest band. The abducting element, which may be a range of motion mechanism, a fixed angle strut or a variable, locked position strut, is fixed at the top end of the lateral upright. The arm section of such braces is variable and may or may not offer control of motion at the elbow. Some of these braces have arm sections which may be extended so that they may be fitted to patients of varying size.

Straps attached to the waist band and chest band secure the brace onto the body and this arrangement, in conjunction with the arm element of the orthosis, generally provides adequate prevention of circumferential migration about the torso. Such braces are lined with padding to minimise any discomfort from hard components lying close to the body surface and the arm sections typically have paddles or shells which, in conjunction with suitable straps, have the effect of stabilizing the arm within the orthosis.

Most braces of this generic type do not compensate for the highly variable geometry of the human torso which, when seen from front or back, may range from the profound "V" of the athlete or model to the ovoid of an obese person.

One modern shoulder brace which does so compensate is the subject of U.S. Pat. No. 5,033,461 granted to one of the present authors (D.E. Young) and K.P. Davis. This brace is sold commercially under the name of Masterhinge® Shoulder Brace. The compensating mechanism is in the form of a hinged arrangement between the lateral upright and the waist band. The hinge is basically of the single axis yoke type with the axis designed to lie in the horizontal plane and directed antero-posteriorally. Another brace featuring such a hinge arrangement between the waist band and the lateral upright has recently been reported to the present authors from the U.S.A. but this has not been positively identified.

Patient intolerance and compliance towards shoulder braces is a problem because although they function well during the day and whilst the patient is upright, they are uncomfortable when the patient sits or lies down. Even when the patient rests propped up by several pillows, there is a tendency for the front of the waist band to dig in to either the lower abdomen, the upper front aspect of the thigh or the inguinal area, causing discomfort and often disturbed sleep. Because it is very difficult for the patient to avoid loading such a brace in a manner and to an extent which is outside its primary purpose, deleterious effects on components over an extended period of use should be considered.

It has been conventional thinking, amongst those skilled in the art, that to try to introduce relative motion waist band and the lateral upright in a shoulder brace would lead to loss of control of flexion and abduction at that joint, thus risking compromise of the outcome of recent surgery or alternatively to unacceptable loss of rotational stability of the orthosis at the waist. A number of investigations led the present authors to the conclusion that this need not be the case.

The present invention provides improvements to upper body orthoses for the shoulder or arm, used following injury or surgery, in which a novel arrangement between a lateral upright and a waist band provides means for enhancing patient comfort, especially during sitting and lying down and which, additionally, considerably reduces the loads in this area to which prior art braces are subject. Furthermore, trials have shown that when orthoses according to the present invention are properly fitted, control of the shoulder is well maintained and loss of stability does not occur.

According to the present invention there is provided a mechanism for improving any orthosis for the upper limb which includes a rigid lateral upright member attached at its lower end to a waist band or plate and near its upper end to a chest band or plate and an arm section comprising at least a strut provided with means to support and stabilise the arm. It is to be understood that any orthosis of the type under consideration will have the waist band, chest band and arm support means lined with suitable pads to enhance comfort and will also be provided with securing strap means in order that the orthosis may be attached to the patient. In such an orthosis connection between the torso section and the arm section may be in the form of a fixed angle strut or a variable locked position strut or alternatively an abducting mechanism, which may be a range of motion device. Further, the arm section may optionally incorporate a hinge at the elbow which may be unrestricted or which may offer control of motion.

According to the invention, the mechanism of connection between the rigid lateral upright member and the waist band of an upper body orthosis is effected by the provision of joint means wherein a first element is in the form of a suitable mount, conveniently formed in metal such as stainless steel and attached to the waist band and wherein a central portion extends laterally and terminates in a bearing which is a modified sphere.

A second element comprises an upwardly directed stem provided with a downwards extension terminating in an annulus. The annulus is provided with a bearing having an inner surface which substantially defines a spherical zone which is so sized that its fits intimately over and onto the spherical portion of the first element in a generally antero-posterior alignment so as to provide a spherical joint.

A third element comprises a mounting block which is attached to or integral with the lower end of the lateral upright member of the upper body orthosis and is adapted by the provision of a circular hole, the axis of which is parallel to the long axis of the lateral upright, to receive and retain the upwardly directed stem of the second element. The stem of the second element and the hole of the third element are mutually adapted to fit intimately and rotatably together such as to provide a pivotal joint.

The mechanism of the connection between the waist band and the lateral upright of the upper body orthosis of the present invention thus provides for substantially unrestricted rotation in a pivotal joint (when the orthosis is not fitted to a patient) about an axis disposed on or parallel and closely spaced apart from the long axis of the lateral upright and which is generally vertical during standing. The mechanism also provides for substantially unrestricted antero-posterior travel in a spherical joint about a horizontal axis normal to the mount of the first element and which lies on a diameter of the modified sphere bearing and also passes centrally through the laterally extending central portion.

It is, therefore, an object of this invention to provide an orthosis for the upper body which is substantially unrestricted over the physiological range of motion likely to occur at the waist, such as during bending, sitting or lying and which will offer the benefit of enhanced comfort for the patient.

It is another object of this invention to provide an orthosis for the upper body which can compensate for variation in the shape of the human torso achieved by virtue of travel at a spherical joint, towards or away from the waist band during the fitting and strapping procedure.

It is yet another object of this invention to eliminate significant tractive, compressive and torque loads between the lateral upright member (together with its associated structures) and the waist band assembly.

Other features, objects and advantages will become apparent from the specification and drawings.

DETAILED DESCRIPTION OF PREFERRED EMBODIMENTS

Figure 1:
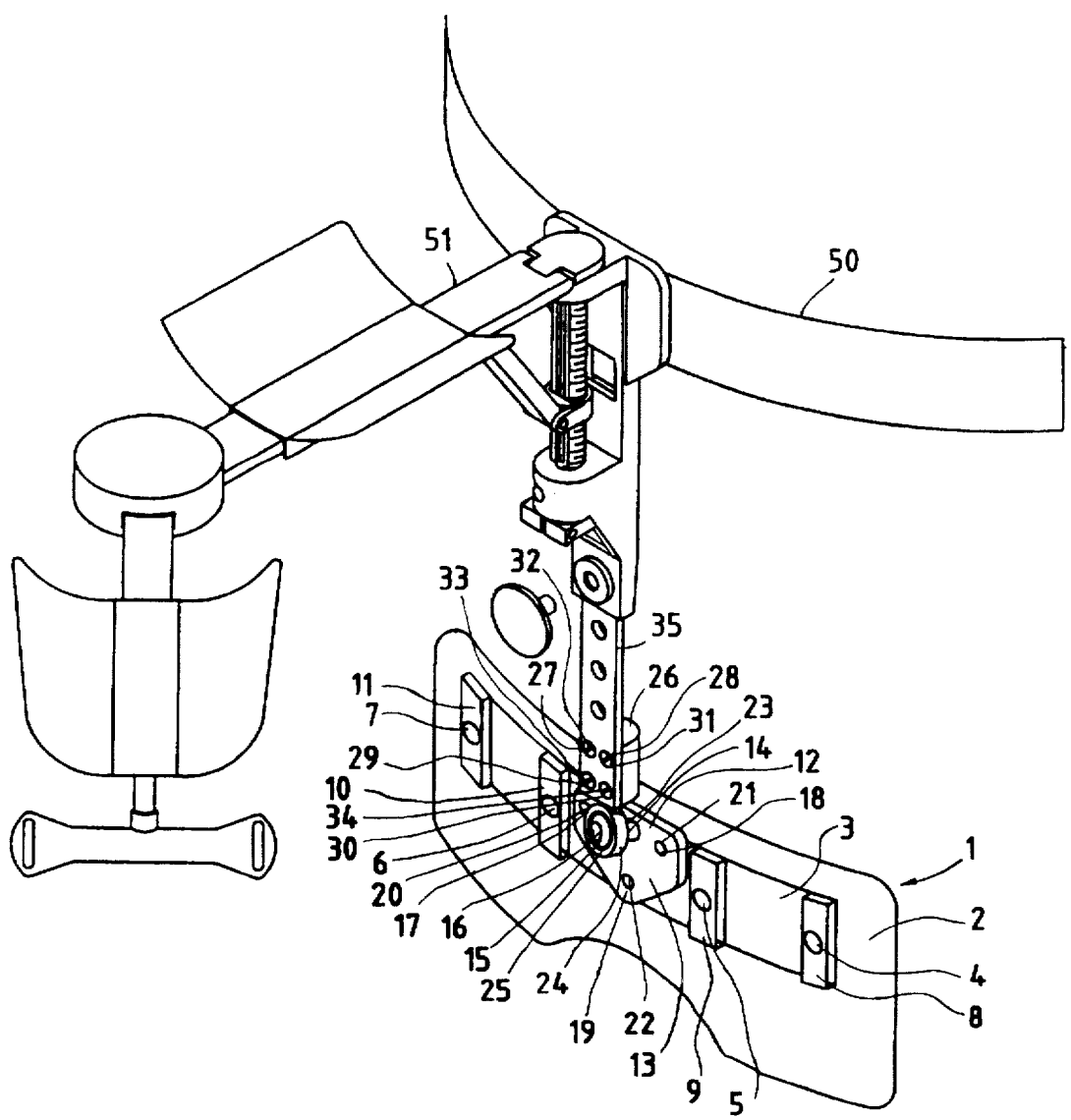
FIG. 1 is a general perspective view of an improved upper body orthosis for the shoulder and arm, according to the invention, with straps and padding omitted.

Referring first to FIG. 1, an orthosis 1 for the upper limb has a partial waist band 2 die-cut from plastics and fitted along its mid-line with a reinforcing strip 3 preferably made in a formable grade of stainless steel. Attachment means in the form of rivets 4–7 secure reinforcing strip 3 to waist band 2 and also serve to retain guides 8–11 for a circumferential strap (omitted) used to secure the orthosis about the patient's waist. A mount 12 is attached centrally to partial waist band 2 and comprises a load spreading plate 13 and a lateral extension 14. Lateral extension 14 terminates in a substantially spherical bearing portion 15 flattened near its most lateral extent and provided with a counter-bored hole adapted with thread means to receive screw 16. Mount 12 is provided with holes 17–19 and attachment means between it and reinforcing strip 3 are provided in the form of rivets 20–22.

A stem 23 preferably made in metal, is of substantially circular cross-section and is adapted at its lower end to form an annulus 24. Annulus 24 constitutes a journal and is fitted with a suitable hard bearing 25 the inner surface of which substantially defines a spherical zone and is so sized and adapted that it fits intimately and securely over and onto the surface of spherical bearing portion 15 of mount 12. This arrangement constitutes a first joint which is a spherical joint.

Stem 23 engages intimately, slidingly and rotatably with a mounting block 26 which is adapted to receive it. This arrangement constitutes a linkage and a second joint which is a pivotal joint.

Mounting block 26 is further adapted by the provision of blind holes 27–30 having thread means to accept attachment means in the form of screws 31–34 which are used to secure it in axial alignment to lateral upright 35 conveniently made in steel. It is to be understood that the provision of mounting block 26 as a separate component secured by screws 31–34 is preferred for ease of manufacturing only and that its function could be achieved by the provision of a single integrated component, made by machining or casting, combining the principal features of 26 and 35.

The remaining parts of the orthosis of the preferred embodiment are in accordance with U.S. Pat. No. 5,033,461 to Young and Davis. As disclosed in that patent, such an orthosis includes an upper chest band or plate connected to the upper end of a rigid lateral upright member and an arm section having a strut with means to support and stabilize a wearer's arm. Such an upper chest band or plate is generally designated herein by numeral 50, and an arm supporting section by numeral 51, in FIG. 1.

Figure 2:
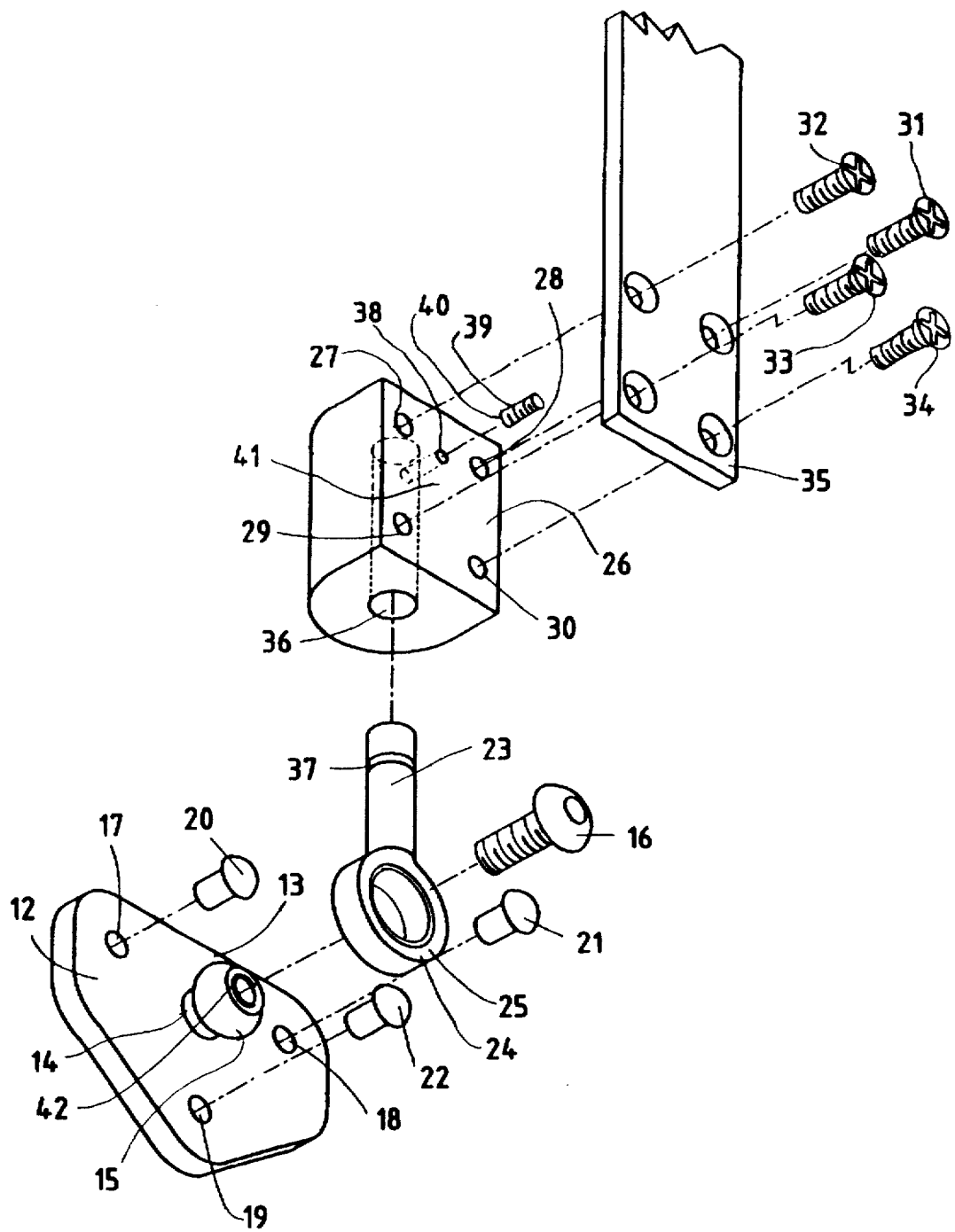
FIG. 2 is an exploded perspective view of a first preferred embodiment of the mechanism for attaching the lateral upright to the waist band reinforcing strip.

In FIG. 2, it may be seen, additionally, that the adaptation of mounting block 26 to receive stem 23 is in the form of a substantially circular hole 36 the axis of which is in parallel alignment to the long axis of lateral upright 35. Stem 23 has a circumferential groove 37. When stem 23 is correctly engaged in hole 36 groove 37 lies beneath hole 38 in mounting block 26. Hole 38 extends into hole 36 and is provided with thread means to receive set screw 39 which is of such a length that when its lower end 40 engages groove 37 it lies just under-flush with respect to surface 41 of mounting block 26, thereby providing retaining means for stem 23 within mounting block 26. Set screw 39 is so sized and positioned that it allows stem 23 to rotate around its principal axis within hole 36 of mounting block 26 constituting a pivotal joint. In the assembled condition, annulus 24 is ultimately restrained and retained upon spherical bearing 15 by the threaded engagement of screw 16 within counterbored hole 42.

Figure 3:
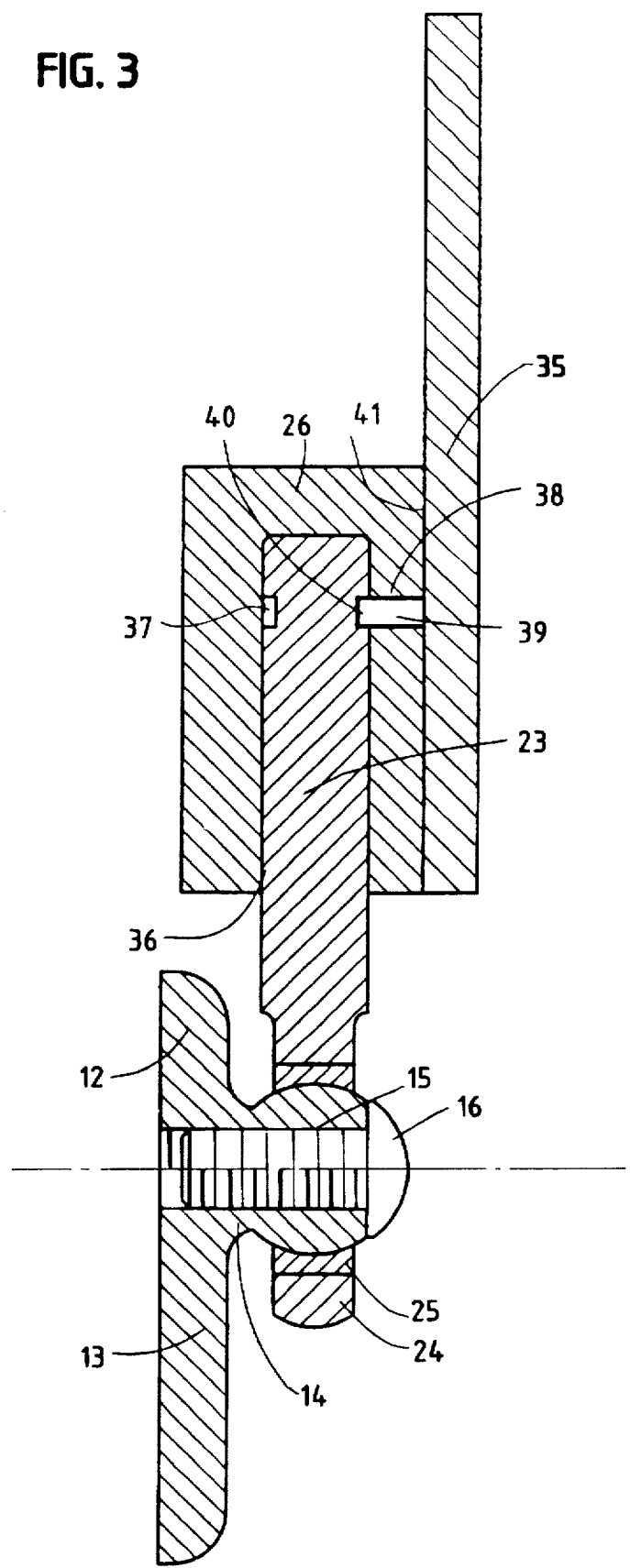
FIG. 3 is a section of the assembled mechanism of a first preferred embodiment for attaching the lateral upright to the waist band reinforcing strip.

In FIG. 3, the mechanism described with reference to FIG. 2, is shown assembled, in section.

In all important aspects, the external appearance and the majority of components of the second preferred embodiment are indistinguishable from the first preferred embodiment.

Figure 4:
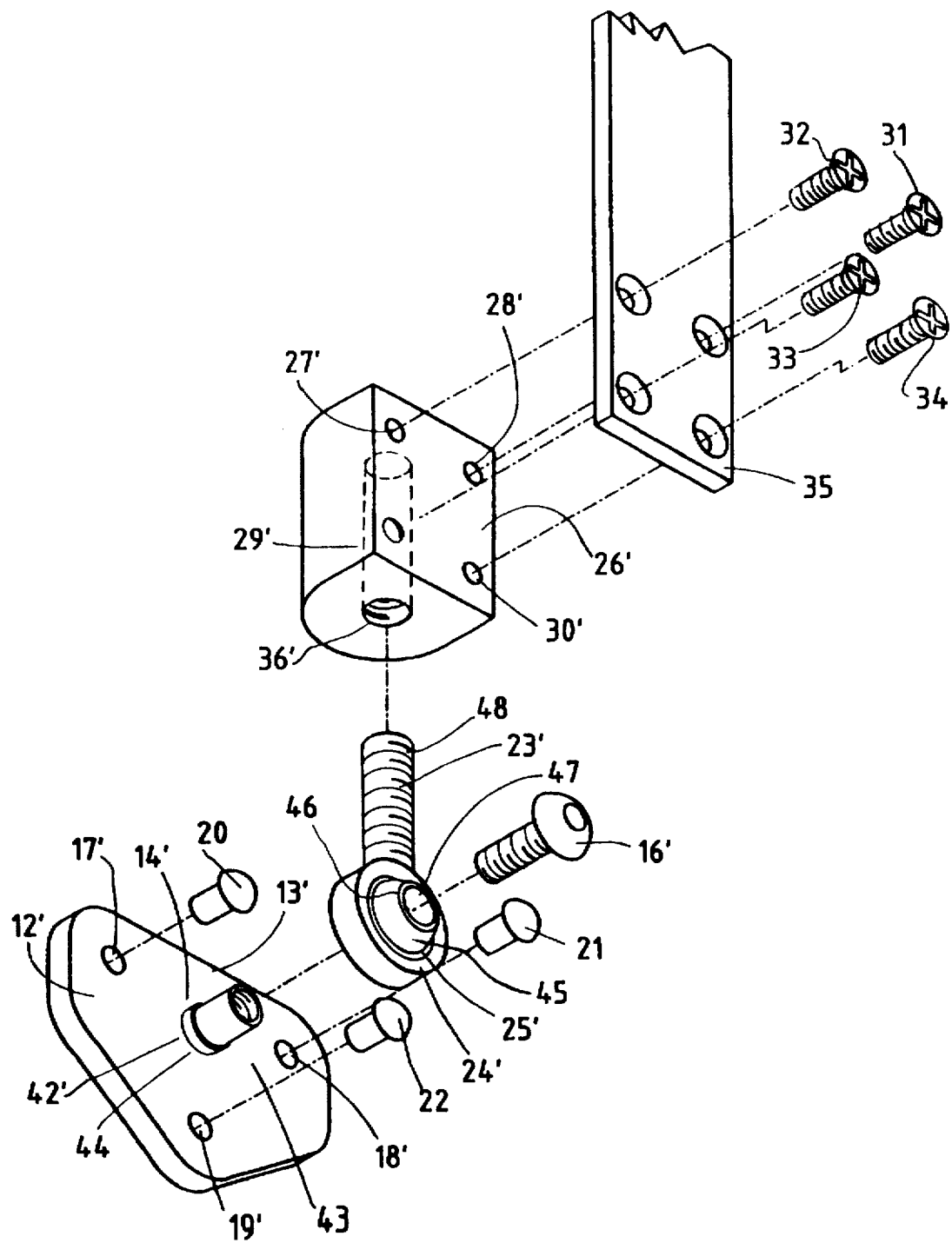
FIG. 4 is an exploded perspective view of a second preferred embodiment of the mechanism for attaching the lateral upright to the waist band reinforcing strip.

However, as may be seen by reference to FIG. 4, details of mount 12', stem 23' and mounting block 26' differ. Mount 12' comprises a load spreading plate 13' and a lateral extension 14'. In this embodiment, lateral extension 14' is a substantially cylindrical spigot 43 with a shouldered portion 44 provided with a counter-bored hole 42' adapted with thread means to receive screw 16'. Mount 12' is provided with holes 17'–19' and attachment means between it and reinforcing strip 3 of FIG. 1, are provided in the form of rivets 20'22.

Stem 23' is adapted at its lower end to form annulus 24'. Annulus 24' is fitted with a suitable hard bearing 25' the inner surface of which substantially defines a spherical zone and is so sized and adapted that it fits intimately and securely over and onto part of the surface of a modified spherical bearing 45. Modified spherical bearing 45 has two parallel flat faces (of which only 46 may be seen) the centers of which lie on a diameter which is also the axis of a substantially cylindrical through hole 47. Hole 47 in modified spherical bearing 45 fits intimately and slidingly over spigot 43 and is retained there by screw 16' which also restrains annulus 24'. This arrangement constitutes the first joint of the second preferred embodiment which is a spherical joint.

Mounting block 26' is adapted to receive stem 23' by the provision of a substantially circular threaded hole 36' the axis of which is in parallel alignment to the long axis of lateral upright 35. Stem 23' has a male threaded portion 48 which, when correctly engaged with the female thread means of hole 36' allows stem 23' to rotate around its principal axis and ensures its retention therein. Mounting block 26' is further adapted by the provision of blind holes 27'–30' having thread means to accept attachment means in the form of screws 31–34 employed to secure it to lateral upright 35. This arrangement constitutes the linkage and second joint of the second preferred embodiment which is a pivotal joint.

This embodiment has the advantage of allowing the orthosis to be packed and shipped more easily, however, there is a requirement for stem 23' to be assembled to mounting block 26' prior to use.

Figure 5:
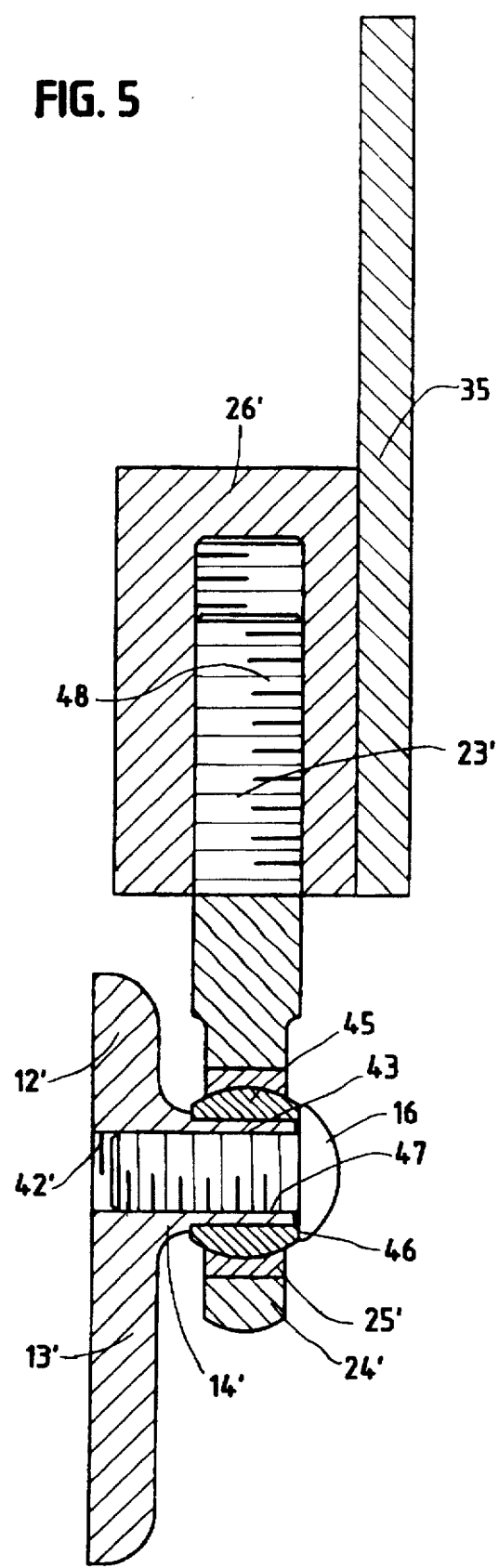
FIG. 5 is a section of the assembled mechanism of a second preferred embodiment for attaching the lateral upright to the waist band reinforcing strip.

In FIG. 5, the mechanism described with reference to FIG. 4, is shown assembled, in section.

We contemplate and have made other, less preferred embodiments, including inversions of the two preferred embodiments described above.

The first joint which is a partial sphere, will allow a large range of free motion forwards and backwards (with respect to the vertical or standing position) around that part of it which has a full circumference. This is disposed about a substantially horizontal axis which is normal to mount 12, 12' and which lies on a diameter of the modified spherical bearing 15, 45 and which also passes centrally through lateral extension 14, 14'.

When worn by a patient, this axis is effectively normal to the lateral aspect of the waist of the wearer on the side under treatment and the motion of the joint makes sitting and lying down very easy. The instant invention is in marked contradistinction to prior art orthoses where the connection between waist band and upright is fixed and and unyielding, making bending difficult and uncomfortable.

In addition the disposition of the first joint will allow that part of the orthosis above it to accommodate a wide variation in the shape of a torso by virtue of motion over part of the circumference of the sphere, which occurs towards or away from the waist band, during the fitting and strapping procedure.

The first joint is also capable of some rotation and we prefer a zonal spherical joint to a ball and socket spherical joint because this motion and the accommodative range are greater, in this context, with the zonal solution.

The provision of the generally upwardly directed second, pivotal, joint allows that portion of the orthosis above the waist band to rotate freely when it is off the patient. However, during use, the upper part of the orthosis is secured on the patient's upper torso by a chest strap and also about the arm by further straps. Furthermore the chest and arm portions are linked and this overall arrangement stabilizes the orthosis in position. Thus, during use, the function of the second, pivotal, joint is to eliminate torsional stresses and stress reversals in the orthosis which, in prior art devices, build up rapidly during sitting and other normal movements which involve bending at the waist.

The reactive forces which produce such stresses in prior art devices develop at points of impingement of the orthosis upon the body of the patient and are well known to be sufficient to override the cushioning effect of the padded liners supplied. The effect is manifested as discomfort which can be prolonged and quite severe, especially when sitting down for extended periods. The instant invention eliminates these effects and in addition drastically reduces the risk of fatigue in components.

From the foregoing is can be realized that this invention provides an improved orthosis for the upper limb having a free moving jointed connection between the waist band and lateral upright, greatly improved comfort for the patient and enhanced longevity due to large reductions in stresses on components. Although various embodiments have been illustrated, this was for the purpose of describing but not limiting the invention. Various modifications, which will become apparent to one skilled in the art, are within the scope of this invention described in the attached claims.

We claim:

1. An orthosis for the human upper limb comprising a lower plate adapted to be secured to a wearer's waist directly above the hip; a lateral upright member having upper and lower ends and extending generally vertically when a wearer is standing; and connecting means joining said lower end of said upright member to said lower plate for limited relative movement therebetween; said connecting means comprising first spherical joint means for providing antero-posterior pivotal movement of said upright member about a generally horizontal axis, and also for lateral-medial pivotal movement of said upright member, to accommodate bending of a wearer at the waist and variations in torso shape; said connecting means also comprising second rotational joint means for providing rotation of said upright member about an axis substantially parallel with the long axis thereof; an upper plate connected to said upper end of said upright member and adapted to be secured to the side of a wearer's chest for maintaining said upright member in generally vertical condition when a wearer is standing; and means connected to said upper end of said upright member adjacent said upper plate for supporting a wearer's arm.

2. The orthosis of claim 1 in which said spherical joint means includes a mounting member joined to said plate having a generally spherical bearing extending laterally therefrom; said lateral upright member having an annular bearing at its lower end receiving said spherical bearing.

3. The orthosis of claim 2 in which said second rotational joint means is spaced from and located directly above said spherical joint means.

4. The orthosis of claim 1 in which said second rotational joint means comprises a stem portion having a generally cylindrical outer surface extending upwardly from said annular bearing member; and a mounting block at said lower end of said upright member having a generally cylindrical socket rotatably receiving said stem.

* * * * *